(12) United States Patent
Wang et al.

(10) Patent No.: US 11,428,654 B2
(45) Date of Patent: Aug. 30, 2022

(54) METHOD FOR PREDICTING CORROSION AND SPONTANEOUS COMBUSTION OF SULFUR-RELATED PETROCHEMICAL EQUIPMENT

(71) Applicant: NANJING TECH UNIVERSITY, Nanjing (CN)

(72) Inventors: Zhirong Wang, Nanjing (CN); Shuoxun Shen, Nanjing (CN); Shengping Zhao, Nanjing (CN); Juncheng Jiang, Nanjing (CN); Xue'e Zhao, Nanjing (CN); Zhan Dou, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 305 days.

(21) Appl. No.: 16/958,753

(22) PCT Filed: Oct. 25, 2018

(86) PCT No.: PCT/CN2018/111767
§ 371 (c)(1),
(2) Date: Jun. 29, 2020

(87) PCT Pub. No.: WO2020/062377
PCT Pub. Date: Apr. 2, 2020

(65) Prior Publication Data
US 2020/0333272 A1    Oct. 22, 2020

(30) Foreign Application Priority Data
Sep. 26, 2018 (CN) .......................... 201811121031.7

(51) Int. Cl.
*G01N 25/02* (2006.01)
*G01N 17/04* (2006.01)
(Continued)

(52) U.S. Cl.
CPC ............. *G01N 25/02* (2013.01); *G01N 17/04* (2013.01); *G01N 31/224* (2013.01);
(Continued)

(58) Field of Classification Search
CPC ...... G01N 25/02; G01N 17/04; G01N 31/224; G01N 33/0042; G01N 33/0063;
(Continued)

(56) References Cited

U.S. PATENT DOCUMENTS 4,622,105 A * 11/1986 Liu ..................... G01N 27/4074
204/424
2020/0333272 A1* 10/2020 Wang ..................... G01N 17/04

FOREIGN PATENT DOCUMENTS

CN    101446417 A *  6/2009
CN    101493403 A    7/2009
(Continued)

*Primary Examiner* — Ryan D Walsh
(74) *Attorney, Agent, or Firm* — Zhihua Han; Wen IP LLC

(57) ABSTRACT

Disclosed is a method for predicting corrosion and spontaneous combustion of sulfur-related petrochemical equipment. The method solves the issues in the existing techniques that includes narrow predicting range, high workload in installation and maintenance, and time lag in predicting corrosion and spontaneous combustion inside equipment. The method comprises a step of a dual index system prediction, which includes a step of monitoring a temperature and a step of detecting $SO_2$ gas generated by spontaneous combustion. The time when spontaneous combustion occurs can be accurately calculated by using a fitted quantitative relationship formula generated by the spontaneous combustion of corrosion products. The method has a low Labor cost. The method has a low labor cost and, does not
(Continued)

require on-site gas detection to be carried out by means of manual detection, which both reduces the cost and ensures the detection accuracy.

8 Claims, 2 Drawing Sheets

(51) Int. Cl.
  *G01N 33/00* (2006.01)
  *G01N 31/22* (2006.01)
  *G08B 21/16* (2006.01)
  *G08B 21/18* (2006.01)
  *F02D 35/02* (2006.01)

(52) U.S. Cl.
  CPC ..... *G01N 33/0042* (2013.01); *G01N 33/0063* (2013.01); *C10G 2300/4006* (2013.01); *C10G 2300/4075* (2013.01); *F02D 35/025* (2013.01); *G08B 21/16* (2013.01); *G08B 21/182* (2013.01)

(58) Field of Classification Search
  CPC .... C10G 2300/4006; C10G 2300/4075; F02D 35/025; G08B 21/16; G08B 21/182
  See application file for complete search history.

(56) References Cited

FOREIGN PATENT DOCUMENTS

| | | | | | |
|---|---|---|---|---|---|
| CN | 102200455 | A | * | 9/2011 | |
| CN | 202133421 | U | * | 2/2012 | |
| CN | 203616273 | U | | 5/2014 | |
| CN | 203705376 | U | | 7/2014 | |
| CN | 205426232 | U | * | 8/2016 | |
| CN | 106642531 | A | * | 5/2017 | |
| CN | 106969797 | A | * | 7/2017 | ............. G01D 21/02 |
| CN | 206515321 | U | * | 9/2017 | |
| CN | 207096159 | U | * | 3/2018 | ........... G01N 27/041 |
| CN | 207620848 | U | * | 7/2018 | |
| GB | 2551172 | A | * | 12/2017 | ........... A62B 17/003 |
| JP | 2002062252 | A | * | 2/2002 | |
| RU | 2247987 | C2 | | 3/2005 | |

* cited by examiner

METHOD FOR PREDICTING CORROSION AND SPONTANEOUS COMBUSTION OF SULFUR-RELATED PETROCHEMICAL EQUIPMENT

CROSS REFERENCE TO RELATED APPLICATION

This application is a national stage application of International application number PCT/CN2018/111767, filed Oct. 25, 2018, titled "METHOD FOR PREDICTING CORROSION AND SPONTANEOUS COMBUSTION OF SULFUR-RELATED PETROCHEMICAL EQUIPMENT", which claims the priority benefit of Chinese Patent Application No. 201811121031.7, filed on Sep. 26, 2018, which is hereby incorporated by reference in its entirety.

TECHNICAL FIELD

The invention relates to the field of safety prediction methods, in particular to a method for predicting corrosion spontaneous combustion of sulfur-related petrochemical equipment.

BACKGROUND

Crude oil has been mined for more than 100 years. The current world crude oil consumption continues to increase. The production rate of traditional light and low-sulfur crude oil in North Africa has declined rapidly. The low-density and low-sulfur crude oil in Asia has also decreased further. The weight and Sulphur content of crude oil produced in the Persian Gulf is also increasing. In future, the crude oil in the world will tend to be heavy and sulfur-containing.

The corrosion of active sulfur present in the sulfur-containing oil to oil storage tanks is low-temperature sulfur corrosion. $H_2S$ in active sulfur has no corrosive effect on the inner wall of the storage tanks in a low temperature and dry environment, but it will show extremely strong corrosiveness in the presence of water. As the service time of the storage tanks increase, the effectiveness of the anticorrosion layer on the inner wall surface of the tank wall decreases, resulting in chemical and electrochemical corrosion of the wall surface, resulting in the formation of a mixture mainly composed of FeS. Along with this, the $H_2S$ in the active sulfur further corrodes the tank wall, and slowly forms a sac-shaped or layered material. The material is composed of ferric sulfur compounds, rust compounds, elemental sulfur, and a small amount of water and oil droplets. Among them, oil droplets, elemental sulfur and other flammable iron sulfide solid particles constitute the combustible substance on the inner wall of the storage tanks. In particular, the tops of atmospheric and decompression device, catalytic cracking device, coking device and other devices in oil refineries and their condensing and cooling systems, as well as the tops of sewage gas stripping towers, air cooling parts of sulfidation and dehydrogenation reactors, etc., undergo opening for cleaning, testing and maintenance after equipment shutdown, during which time oxidization and self-heating of ferric sulfur compounds occur frequently.

When a large amount of air enters the gas-phase space inside the equipment, on the one hand, the ferric sulfur compounds quickly oxidize and release a lot of heat. The sac-shaped or layered substances formed on the inner wall of the equipment hinder the heat diffusion, resulting in the accumulation of heat and the formation of spontaneous combustion, and causing combustible substances to combust; on the other hand, a large amount of air and gas volatilized or vaporized from oil products form an environment inducible to fire and explosion, spontaneous combustion from heat accumulation, and the combustion of combustible substances are likely to cause fire and explosion accidents.

At present, methods for the prediction of equipment corrosion spontaneous combustion in the petrochemical industry all have shortcomings: the corrosion products of previous scientific research are mostly single corrosion products, which cannot effectively simulate the ferrosulfide generated in the sulfur-related petrochemical equipment under actual conditions. The temperature measurement method installs the temperature sensor inside the device. Because it uses a point contact, the prediction range is small, and the workload of installation and maintenance is large. In particular, the temperature sensor probe and lead are easily damaged; in the marker gas detection method, If the threshold of the quantification index is set too high, there is a time lag. In the case of a fast oxidation reaction, the prediction of corrosion spontaneous combustion in the equipment is not timely enough; manual detection has a heavy workload and a long interval, and continuous real-time detection cannot be performed.

SUMMARY

A method for predicting corrosion and spontaneous combustion of sulfur-related petrochemical equipment is disclosed, in order to solve the technical problems of narrow prediction range, heavy workload of installation and maintenance, and the prediction time lag in the existing technologies.

A method for predicting corrosion and spontaneous combustion of sulfur-related petrochemical equipment, comprising the steps of using a dual index prediction system that further comprises the step of monitoring a temperature and the step of monitoring $SO_2$ gas generated from spontaneous combustion.

The step of monitoring a temperature comprises:

A. performing real-time temperature measurement using a thermocouple (2) connected on an outer wall of a sulfur-related petrochemical equipment (1), displaying the temperature measurement value on a temperature measuring instrument (3), and transmitting temperature rise data to a temperature parameter data processing device (4);

B. comparing the temperature rise data with a critical temperature rise threshold using the temperature parameter data processing device (4) to determine whether to turn on alarm, and sending a signal to a DCS (Distributed Control System) central control system (5) when turning on alarm is needed;

C. turning on alarm by the DCS central control system (5) after receiving the signal;

The step of monitoring $SO_2$ gas generated from spontaneous combustion comprises:

A. measuring the $SO_2$ gas concentration in the sulfur-related petrochemical equipment (1) by a wireless $SO_2$ gas detector (7) connected to the sulfur-related petrochemical equipment (1), determining a degree of sulfidation in the sulfur-related petrochemical equipment (1) based on the $SO_2$ gas concentration, and transmitting the degree of sulfidation data to a gas concentration parameter data processing device (6);

B. selecting a critical $SO_2$ gas concentration value from a fitted formula corresponding to the degree of sulfidation;

C. comparing the degree of sulfidation data to the critical $SO_2$ gas concentration value from the fitted formula corresponding to the degree of sulfidation to determine whether to turn on alarm, and sending another signal to the DCS central control system (5) when turning on alarm is needed;

D. turning on alarm by the DCS central control system (5) after receiving the other signal.

Preferably, in the step A of the step of monitoring a temperature, the thermocouple (2) is an external sheathed thermocouple.

Preferably, in the step of monitoring a temperature, the critical temperature rise threshold $\Delta T_s$ is calculated from the formula $$\Delta T_s = C_s \Delta T \max$$

wherein $\Delta T_s = C_s$ is the critical temperature rise threshold that predicts the spontaneous combustion fire in the sulfur-related petrochemical equipment (1) and is measured in Celsius;

wherein $C_s$ is a safety control coefficient; more preferably, $C_s=0.5$ is used by default; $C_s=0.2$ to $0.8$ is adopted in large space buildings, which is more than 50 m³ in) volume).

wherein $\Delta T_{max}$ is the maximum temperature rise that is reached in the initial stage of oxidation when a spontaneous combustion fire occurs in the petrochemical equipment (1) under research conditions, $\Delta T_{max}$ is measured in Celsius.

More preferably, wherein $\Delta T_s$ is capped at 30° C., wherein when an internal temperature of the sulfur-related petrochemical equipment (1) is above 30° C., a cooling procedure is activated to lower the temperature of the sulfur-related petrochemical equipment (1).

Preferably, the critical $SO_2$ gas concentration value $\gamma_s$ from the fitted formula corresponding to the degree of sulfidation is calculated as:

$$\gamma_s = \gamma_{max}$$

wherein $\gamma_s$ is critical $SO_2$ gas concentration value that predicts the spontaneous combustion fire in the sulfur-related petrochemical equipment (1) and is measured in mg/ul;

wherein $C_s$ is a safety control coefficient, with a range of 0.2 to 0.8; and wherein $\gamma_{max}$ is the maximum concentration of $SO_2$ gas under research conditions.

Preferably, corrosion status in the sulfur-related petrochemical equipment (1) includes mild sulfidation and advanced sulfidation.

More preferably, providing the following formula that describe the relationship between $SO_2$ gas concentration $\gamma$ and reaction time t;

$$\gamma = -3 \times 10^{-9} t^5 + 2 \times 10^{-7} t^4 - 3 \times 10^{-6} t^3 - 0.0002 t^2 + 0.0055 t - 0.0101 \quad \text{for mild sulfidation;}$$

$$\gamma = -5 \times 10^{-7} t^4 + 4 \times 10^{-5} t^3 - 0.0012 t^2 + 0.0129 t - 0.0125 \quad \text{for advanced sulfidation;}$$

wherein $\gamma$ is $SO_2$ gas concentration in the sulfur-related petrochemical equipment (1), t is reaction time and measured by minutes;

calculating the corresponding time $t_{max}$ when $\gamma$ reaches a maximum value $\gamma_{max}$, by finding the first derivative on both sides of the above formula and assuming $$\frac{dy}{dt} = 0;$$

obtaining $\gamma_{max}$ by substituting $t_{max}$ into the formula;

More preferably, the critical $SO_2$ gas concentration value $\gamma_s$ that predicts the spontaneous combustion fire is set at 0.017 mg/ul in mild sulfidation; and wherein the critical $SO_2$ gas concentration value $\gamma_s$ that predicts the spontaneous combustion fire is set at 0.012 mg/ul in mild sulfidation.

More preferably, the corrosion status in the sulfur-related petrochemical equipment (1) is mild sulfidation when $SO_2$ gas is generated 150 seconds after initial oxidation of the spontaneously combustion; and wherein the corrosion status in the sulfur-related petrochemical equipment (1) is advanced sulfidation when $SO_2$ gas is generated within 150 seconds of initial oxidation of the spontaneously combustion.

As a prediction method for corrosion spontaneous combustion of sulfur-related petrochemical equipment, the present invention has the following beneficial effects:

In the prior art, most of the spontaneous fire monitoring thresholds are selected inadequately, and the prediction of spontaneous combustion in the equipment is inaccurate. The present invention has high accuracy. By fitting the quantitative relationship formula targeted to the spontaneous combustion of corrosion products, the timing for the spontaneous combustion can be calculated more accurately. On the one hand, the labor cost of the present invention is low, and there is no need to presence of human for on-site gas detection, which reduces the cost while ensuring the detection accuracy. On the other hand, the method of the present invention is simple to operate, and the prediction method uses equipment detection and procedure automation, without requiring additional operations by an operator, ensuring detection accuracy and avoiding accidents caused by human error. Finally, the use of online real-time detection, sheathed thermocouple and $SO_2$ gas detector for real-time feedback monitoring, help to ensure constant monitoring of the equipment and timely warning.

DETAILED DESCRIPTION OF THE PREFERRED EMBODIMENTS

The technical solutions of the present invention will be further described below with reference to the drawings and specific examples.

Embodiment I

Figure 1:
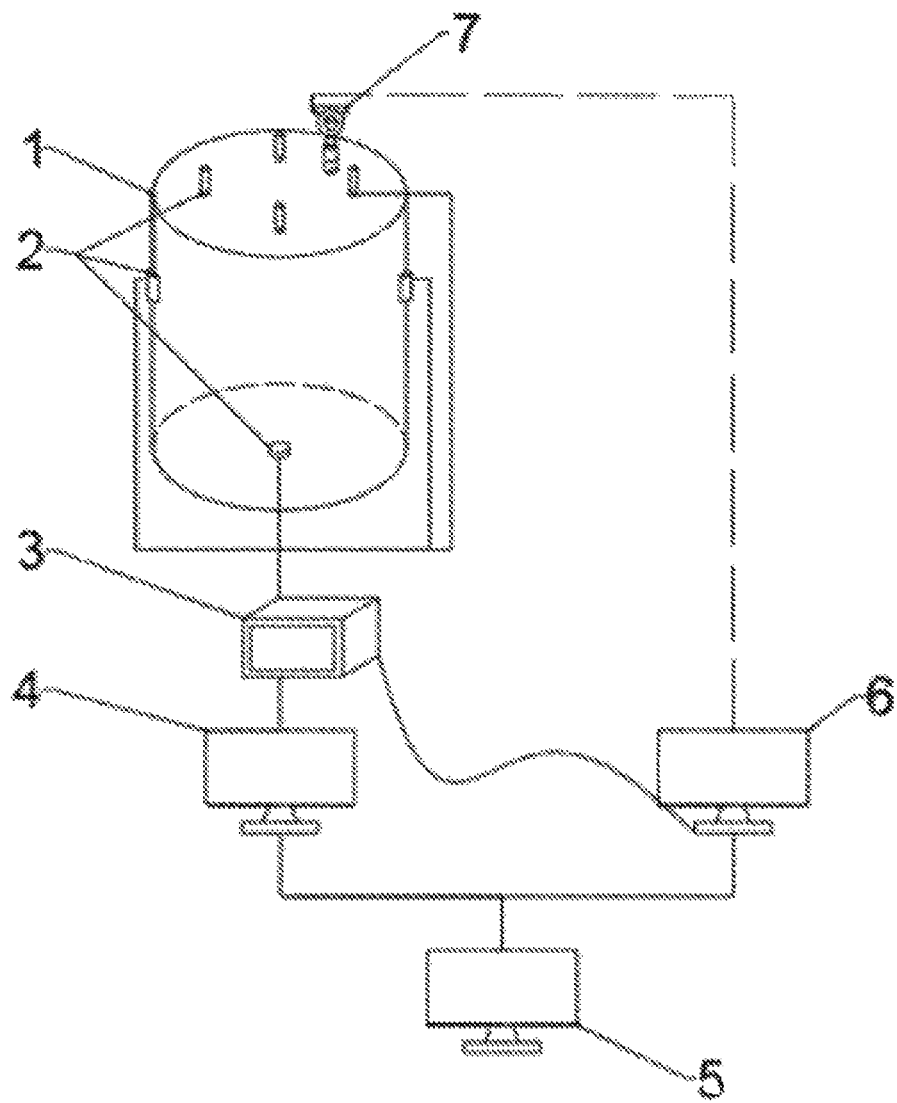
FIG. 1 is a structural diagram showing a system for predicting corrosion and spontaneous combustion of a sulfur-related petrochemical equipment, wherein 1 refers to sulfur-related petrochemical equipment, 2 refers to thermocouple, 3 refers to temperature measuring instrument, 4 refers to temperature parameter data processing device, 5 refers to DCS central control system, 6 refers to gas concentration parameter data processing device, and 7 refers to wireless $SO_2$ gas detector.
Figure 2:
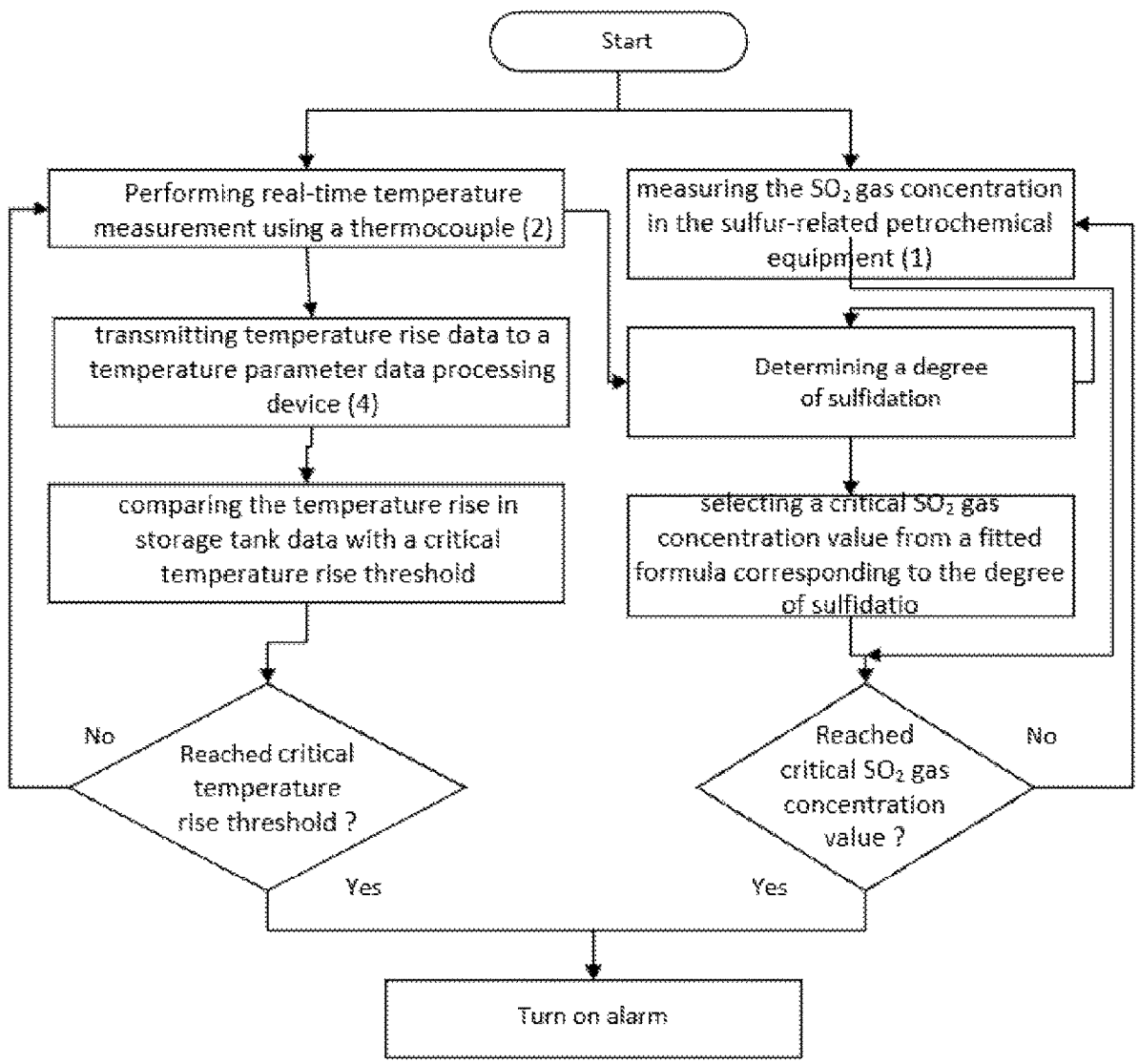
FIG. 2 shows a flow chart of a method for predicting corrosion and spontaneous combustion of a sulfur-related petrochemical equipment.

As shown in FIG. 1 and FIG. 2, the steps of the embodiment are:

1. Based on the size of the floating roof tank, weld a porcelain sleeve with sheathed thermocouple to the bottom of a sulfur-related petrochemical equipment (1) and to the outer wall of the sulfur-related petrochemical equipment (1) corresponding to the corrosion-prone part inside the wall and to the top of the gas phase space. The thermocouple time constant is 15 seconds. The cold terminus of the thermocouple is connected to one end of a compensation wire, and the other end of the compensation wire is connected to a temperature measuring instrument (3). The temperature measuring instrument (3) is connected with a temperature parameter data processing device.

Set the critical temperature rise threshold $\Delta T_s=30°$ C. at the temperature parameter data processing equipment, and obtain real-time temperatures through the thermocouple at parts of the equipment prone to corrosion and spontaneous combustion. When the temperature measured by any thermocouples exceeds the critical temperature rise threshold $\Delta T_s=30°$ C., transmit the time required for the temperature to rise to the critical temperature rise threshold, i.e., the critical time (t $\Delta T_s$), to the DCS system for further processing.

After the corrosion spontaneous combustion occurs, the temperature measuring instrument (3) provides a feedback of the reaction start time, by combining with the time of occurrence of the $SO_2$ gas detected by the wireless $SO_2$ gas detector (7), analysis is performed to determine the degree of sulfidation of the corrosives in the floating roof tank. Choose, according to the degree of sulfidation, a fitted formula describing quantitative relationship between the $SO_2$ gas concentration and time; obtain $\gamma_{max}$, i.e., the maximum concentration of $SO_2$ gas under research conditions, and $\gamma_s$, i.e., critical $SO_2$ gas concentration value. Meanwhile, measure the $SO_2$ gas concentration in the sulfur-related petrochemical equipment (1) in real time using the wireless $SO_2$ gas detector (7), and feedback the $SO_2$ concentration value every 10 seconds through the wireless $SO_2$ gas detector (7). If the measured $SO_2$ gas concentration reaches the critical $SO_2$ gas concentration value, another warning signal is needed, the time required for the storage tank $SO_2$ gas concentration to reach the critical $SO_2$ gas concentration value ($t\gamma_s$) is fed back to the DCS system (5).

When the time required for the temperature to rise to the critical temperature rise threshold, i.e., the critical time (t $\Delta T_s$), is transmitted or fed to the DCS system (5), or when the time required for the storage tank $SO_2$ gas concentration to reach the critical $SO_2$ gas concentration value ($t\gamma_s$) is fed back to the DCS system (5), or when both times are fed back to the DCS system (5), the DNS control phase will turning on an alarm for an early warning that corrosion spontaneous combustion occurs in the floating roof, to provide operators with early warning.

What is claimed is:

1. A method for predicting corrosion and spontaneous combustion of sulfur-related petrochemical equipment, comprising the steps of using a dual index prediction system that further comprises:
    monitoring a temperature, further comprising:
        performing real-time temperature measurement using a thermocouple (2) connected on an outer wall of a sulfur-related petrochemical equipment (1), displaying the temperature measurement value on a temperature measuring instrument (3), and transmitting temperature rise data to a temperature parameter data processing device (4);
        comparing the temperature rise data with a critical temperature rise threshold using the temperature parameter data processing device (4) to determine whether to turn on alarm, and sending a signal to a DCS central control system (5) when turning on alarm is needed; and
        turning on alarm by the DCS central control system (5) after receiving the signal; and
    monitoring $SO_2$ gas generated from spontaneous combustion, further comprising:
        measuring the $SO_2$ gas concentration in the sulfur-related petrochemical equipment (1) by a wireless $SO_2$ gas detector (7) connected to the sulfur-related petrochemical equipment (1), determining a degree of sulfidation in the sulfur-related petrochemical equipment (1) based on the $SO_2$ gas concentration, and transmitting the degree of sulfidation data to a gas concentration parameter data processing device (6);
        selecting a critical $SO_2$ gas concentration value from a fitted formula corresponding to the degree of sulfidation;
        using the gas concentration parameter data processing device (6), comparing degree of sulfidation data to the critical $SO_2$ gas concentration value from the fitted formula corresponding to the degree of sulfidation to determine whether to turn on alarm, and sending another signal to the DCS central control system (5) when turning on alarm is needed; and
        turning on alarm by the DCS central control system (5) after receiving the signal or the another signal;
    wherein the critical temperature rise threshold $\Delta T_s$, is calculated from the formula $$\Delta T_s = C_s \Delta T_{max}$$

wherein $\Delta T_s$ is the critical temperature rise threshold that predicts the spontaneous combustion fire in the sulfur-related petrochemical equipment (1) and is measured in Celsius;
    wherein $C_s$ is a safety control coefficient; more preferably, $C_s=0.5$ is used by default; $C_s=0.2$ to 0.8 is adopted in large space buildings; and
    wherein $\Delta T_{max}$ is the maximum temperature rise that is reached in the initial stage of oxidation when a spontaneous combustion fire occurs in the petrochemical equipment (1), $T_{max}$ is measured in Celsius.

2. The method for predicting corrosion and spontaneous combustion of sulfur-related petrochemical equipment according to claim 1, wherein $\Delta T_s$ is capped at 30° C., wherein when an internal temperature of the sulfur-related petrochemical equipment (1) is above 30° C., a cooling procedure is activated to lower the temperature of the sulfur-related petrochemical equipment (1).

3. The method for predicting corrosion and spontaneous combustion of sulfur-related petrochemical equipment according to claim 1, wherein the critical $SO_2$ gas concentration value $\gamma_s$ from the fitted formula corresponding to the degree of sulfidation is calculated as:

$$\gamma_s = C_s \gamma_{max}$$

wherein $\gamma_s$ is critical $SO_2$ gas concentration value that predicts the spontaneous combustion fire in the sulfur-related petrochemical equipment (1) and is measured in mg/ul;
    wherein $C_s$ is a safety control coefficient, with a range of 0.2 to 0.8; and
    wherein $\gamma_{max}$ is the maximum concentration of $SO_2$ gas.

4. The method for predicting corrosion and spontaneous combustion of sulfur-related petrochemical equipment according to claim 3, wherein corrosion status in the sulfur-related petrochemical equipment (1) includes mild sulfidation and advanced sulfidation.

5. The method for predicting corrosion and spontaneous combustion of sulfur-related petrochemical equipment according to claim 4, further comprising:
providing the following fitted formula that describe the relationship between $SO_2$ gas concentration γ and reaction time t;

$\gamma=-3\times10^{-9}t^5+2\times10^{-7}t^4-3\times10^{-6}t^3-0.0002t^2+0.0055t-0.0101$ for mild sulfidation;

$\gamma=-5\times10^{-7}t^4+4\times10^{-5}t^3-0.0012t^2+0.0129t-0.0125$ for advanced sulfidation;

wherein γ is $SO_2$ gas concentration in the sulfur-related petrochemical equipment (1), t is reaction time and measured by minutes;
calculating the corresponding time $t_{max}$ when γ reaches a maximum value $\gamma_{max}$, by finding the first derivative on both sides of the above formula and assuming $$\frac{dy}{dt}=0;$$

obtaining $\gamma_{max}$ by substituting ta into the formula;
wherein the critical $SO_2$ gas concentration value $\gamma_s$ that predicts the spontaneous combustion fire is set at 0.017 mg/ul in mild sulfidation; and
wherein the critical $SO_2$ gas concentration value $\gamma_s$ that predicts the spontaneous combustion fire is set at 0.012 mg/ul in advanced sulfidation.

6. The method for predicting corrosion and spontaneous combustion of sulfur-related petrochemical equipment according to claim 1, wherein corrosion status in the sulfur-related petrochemical equipment (1) includes mild sulfidation and advanced sulfidation.

7. The method for predicting corrosion and spontaneous combustion of sulfur-related petrochemical equipment according to claim 6, further comprising:
providing the following fitted formula that describes the relationship between $SO_2$ gas concentration γ and reaction time t;

$\gamma=-3\times10^{-9}t^5+2\times10^{-7}t^4-3\times10^{-6}t^3-0.0002t^2+0.0055t-0.0101$ for mild sulfidation;

$\gamma=-5\times10^{-7}t^4+4\times10^{-5}t^3-0.0012t^2+0.0129t-0.0125$ for advanced sulfidation;

wherein γ is $SO_2$ gas concentration in the sulfur-related petrochemical equipment (1), t is reaction time and measured by minutes;
calculating the corresponding time $t_{max}$ when γ reaches a maximum value $\gamma_{max}$ by finding the first derivative on both sides of the above formula and assuming $$\frac{dy}{dt}=0;$$

obtaining $\gamma_{max}$ by substituting $t_{max}$ into the formula;
wherein the critical $SO_2$ gas concentration value $\gamma_s$ that predicts the spontaneous combustion fire is set at 0.017 mg/ul in mild sulfidation; and
wherein the critical $SO_2$ gas concentration value $\gamma_s$ that predicts the spontaneous combustion fire is set at 0.012 mg/ul in advanced sulfidation.

8. The method for predicting corrosion and spontaneous combustion of sulfur-related petrochemical equipment according to claim 6, wherein the corrosion status in the sulfur-related petrochemical equipment (1) is mild sulfidation when $SO_2$ gas is generated 150 seconds after initial oxidation of the spontaneously combustion; and
wherein the corrosion status in the sulfur-related petrochemical equipment (1) is advanced sulfidation when $SO_2$ gas is generated within 150 seconds of initial oxidation of the spontaneously combustion.

* * * * *